US 9,968,791 B2

(12) United States Patent
Aghassian

(10) Patent No.: US 9,968,791 B2
(45) Date of Patent: May 15, 2018

(54) EXTERNAL CHARGER FOR AN IMPLANTABLE MEDICAL DEVICE SYSTEM HAVING A COIL FOR COMMUNICATION AND CHARGING

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 240 days.

(21) Appl. No.: 14/967,826

(22) Filed: Dec. 14, 2015

(65) Prior Publication Data

US 2016/0096028 A1 Apr. 7, 2016

Related U.S. Application Data

(63) Continuation of application No. 13/647,200, filed on Oct. 8, 2012.
(Continued)

(51) Int. Cl.
 *A61N 1/372* (2006.01)
 *A61N 1/378* (2006.01)

(52) U.S. Cl.
 CPC ....... *A61N 1/37223* (2013.01); *A61N 1/3787* (2013.01); *A61N 1/37235* (2013.01); *A61N 1/37247* (2013.01); *A61N 1/37252* (2013.01)

(58) Field of Classification Search
 CPC .......................... A61N 1/37223; A61N 1/3787
 See application file for complete search history.

(56) References Cited

U.S. PATENT DOCUMENTS

2005/0004619 A1* 1/2005 Wahlstrand .......... A61N 1/3787
 607/45
2009/0118796 A1 5/2009 Chen et al.
 (Continued)

FOREIGN PATENT DOCUMENTS

JP 2002-315209 10/2002

OTHER PUBLICATIONS

Partial International Search Report regarding application No. PCT/US2012/062393 dated Apr. 24, 2013.

*Primary Examiner* — William Levicky
(74) *Attorney, Agent, or Firm* — Lewis, Reese & Nesmith, PLLC

(57) ABSTRACT

Disclosed in an improved medical implantable device system including an improved external charger that is able to communicate with an external controller and IPG using the communication protocol (e.g., FSK) used to implement communications between the external controller and the implant. The external controller as modified uses its charging coil to charge the implant, and also to communicate with the other devices in the system. As such, the external charger is provided with transceiver circuitry operating in accordance with the protocol, and also includes tuning circuitry to tune the coil as necessary for communications or charging. Communication or charging access to the charging coil in the external charger is time multiplexed. The disclosed system allows charging information to be provided to the user interface of the external controller so that it can be reviewed by the user, who may take corrective action if necessary. Also disclosed are schemes for synchronizing and arbitrating communications between the devices in the system.

20 Claims, 12 Drawing Sheets

Related U.S. Application Data

(60) Provisional application No. 61/558,601, filed on Nov. 11, 2011.

(56) References Cited

U.S. PATENT DOCUMENTS

| | | | |
|---|---|---|---|
| 2009/0216296 A1* | 8/2009 | Meskens | A61N 1/3787 607/57 |
| 2010/0069992 A1* | 3/2010 | Aghassian | A61N 1/3787 607/32 |
| 2010/0179618 A1 | 7/2010 | Marnfeldt et al. | |
| 2010/0204756 A1 | 8/2010 | Aghassian | |
| 2010/0305663 A1 | 12/2010 | Aghassian | |
| 2011/0112610 A1 | 5/2011 | Rahman et al. | |
| 2011/0112611 A1 | 5/2011 | Aghassian | |
| 2011/0137378 A1 | 6/2011 | Klosterman et al. | |

* cited by examiner

EXTERNAL CHARGER FOR AN IMPLANTABLE MEDICAL DEVICE SYSTEM HAVING A COIL FOR COMMUNICATION AND CHARGING

CROSS-REFERENCE TO RELATED APPLICATIONS

This is a continuation application of U.S. patent application Ser. No. 13/647,200, filed Oct. 8, 2012, which is a non-provisional of U.S. Provisional Patent Application Ser. No. 61/558,601, filed Nov. 11, 2011. Priority is claimed to both of these applications, and both are incorporated herein by reference.

FIELD OF THE INVENTION

The present invention relates to an improved implantable medical device system having a communication link between an external controller and an external charger.

BACKGROUND

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system. For example, the disclosed invention can also be used with a Bion™ implantable stimulator, such as is shown in U.S. Patent Publication 2007/0097719, or with other implantable medical devices.

As shown in FIGS. 1A and 1B, a SCS system typically includes an Implantable Pulse Generator (IPG) 100, which includes a biocompatible device case 30 formed of titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102 and 104 couple to the IPG 100 using lead connectors 38a and 38b, which are fixed in a header material 36, which can comprise an epoxy for example. In a SCS application, electrode leads 102 and 104 are typically implanted on the right and left side of the dura within the patient's spinal cord. These leads 102 and 104 are then tunneled through the patient's flesh to a distant location, such as the buttocks, wherein the IPG 100 is implanted.

As shown in cross section in FIG. 3, the IPG 100 typically includes an electronic substrate assembly 14 including a printed circuit board (PCB) 16, along with various electronic components 20, such as a microcontroller, integrated circuits, and capacitors mounted to the PCB 16. Two coils are generally present in the IPG 100: a telemetry coil 13 used to transmit/receive data to/from an external controller 12; and a charging coil 18 for charging or recharging the IPG's battery 26 using an external charger 50. The telemetry coil 13 can be mounted within the header 36 of the IPG 100 as shown.

FIG. 2 shows plan views of the external controller 12 and the external charger 50, and FIG. 3 shows these external devices in cross section and in relation to the IPG 100 with which they communicate. The external controller 12, such as a hand-held programmer or a clinician's programmer, is used to send data to and receive data from the IPG 100. For example, the external controller 12 can send programming data such as therapy settings to the IPG 100 to dictate the therapy the IPG 100 will provide to the patient. Also, the external controller 12 can act as a receiver of data from the IPG 100, such as various data reporting on the IPG's status. As shown in FIG. 3, the external controller 12, like the IPG 100, also contains a PCB 70 on which electronic components 72 are placed to control operation of the external controller 12. The external controller 12 is powered by a battery 76, but could also be powered by plugging it into a wall outlet for example. A telemetry coil 73 is also present in the external controller 12, which coil will be discussed further below.

The external controller 12 typically comprises a user interface 74 similar to that used for a portable computer, cell phone, or other hand held electronic device. The user interface 74 typically comprises touchable buttons 80 and a display 82, which allows the patient or clinician to send therapy programs to the IPG 100, and to review any relevant status information reported from the IPG 100.

Wireless data transfer between the IPG 100 and the external controller 12 preferably takes place via inductive coupling. This typically occurs using a well-known Frequency Shift Keying (FSK) protocol, in which logic '0' bits are modulated at a first frequency (e.g., 121 kHz), and logic '1' bits are modulated at a second frequency (e.g., 129 kHz). To implement such communications, both the IPG 100 and the external controller 12 have coils 13 and 73 respectively. Either coil can act as the transmitter or the receiver, thus allowing for two-way communication between the two devices. Referring to FIG. 4, when data is to be sent from the external controller 12 to the IPG 100 (FSK link 170), coil 73 is energized with alternating current (AC), which generates a magnetic field, which in turn induces a voltage in the IPG's telemetry coil 13. The generated magnetic field is FSK modulated (120) in accordance with the data to be transferred. The induced voltage in coil 13 can then be FSK demodulated (125) at the IPG 100 back into the telemetered data signals. Data telemetry in the opposite direction (FSK link 172) from IPG 100 to external controller 12 occurs similarly. This means of communicating by inductive coupling is transcutaneous, meaning it can occur through the patient's tissue 25.

The external charger 50 is used to charge (or recharge) the IPG's battery 26. Specifically, and similarly to the external controller 12, the external charger 50 contains a coil 88 which is energized via charging circuit 122 with a non-modulated AC current to create a magnetic charging field (174). This magnetic field induces a current in the charging coil 18 within the IPG 100, which current is rectified (132) to DC levels, and used to recharge the battery 26, perhaps via a charging and battery protection circuit 134 as shown. The frequency of the magnetic charging field (e.g., 80 kHz) may differ from that used for FSK telemetry (nominally 125 kHz). Again, inductive coupling of power in this manner occurs transcutaneously.

The IPG 100 can also communicate data back (176) to the external charger 50 using Load Shift Keying (LSK) modulation circuitry 126. LSK modulation circuitry 126 receives data to be transmitted back to the external charger 50 from the IPG's microcontroller 150, and then uses that data to modulate the impedance of the charging coil 18. In the illustration shown, impedance is modulated via control of a load transistor 130, with the transistor's on-resistance providing the necessary modulation. This change in impedance is reflected back to coil 88 (LSK link 176) in the external charger 50, which interprets the reflection at LSK demodulation circuitry 123 to recover the transmitted data. This means of transmitting data from the IPG 100 to the external charger 50 is useful to communicate data relevant to charging of the battery 26 in the IPG 100, such as the battery level, whether charging is complete and the external charger can cease, and other pertinent charging variables. However, because LSK works on a principle of reflection, such data can only be communicated from the IPG 100 to the external charger 50 during periods in which the external charger 50 is active and is producing a magnetic charging field (174).

As shown in FIG. 3, the external charger 50 generally comprises at least one printed circuit board 90, electronic components 92 which control operation of the external charger 50, and a battery 96 for providing operational power for the charger 50 and for the production of the magnetic charging field. Like the external controller 12, the external charger 50 has a user interface 94 to allow the patient or clinician to operate the charger 50. The user interface 94 typically comprises an on/off switch 95 which activates the production of the magnetic charging field; an LED 97 to indicate the status of the on/off switch 95; and a speaker 98 for emitting a "beep" at various times. For example, the speaker 98 can beep if the charger 50 detects that its coil 88 is not in good alignment with the charging coil 18 in the IPG 100. Alignment information can be determined and indicated to the external charger 252 by alignment circuitry 103, which is well-known in the art. In a SCS application in which the IPG 100 is implanted in the patient's buttocks, the external charger 50 is generally positioned behind the patient and held against the patient's skin or clothes and in good alignment with the IPG 100 by a belt or an adhesive patch, which allows the patient some mobility while charging.

As one might appreciate from the foregoing description, the user interface 94 of the external charger 50 is generally simpler than the user interface 74 of the external controller 12. Such user interface simplicity is understandable for at least two reasons. First is the relative simplicity of the charging function the external charger 50 provides. Second, a complicated user interface, especially one having visual aspects, may not be warranted because the external charger 50 may not be visible to the patient when it is used. For example, in a SCS application, the external charger 50 would generally be behind the patient to align properly with the IPG 100 implanted in the buttocks as just discussed. The external charger 50 would not be visible in this position, and thus providing the user interface 94 of the external charger 50 with a display or other visual indicator would be of questionable benefit. Additionally, the external charger 50 may be covered by clothing, again reducing the utility of any visual aspect to the user interface.

Although the simplicity of the user interface 94 of the external charger 50 is understandable, the inventor still finds such simplicity regrettable. Even if operation of the external charger 50 is relatively simple, the fact remains that several pieces of information relevant to the charging process might be of interest to the patient, which charging information is impractical or impossible to present by audible means such as through speaker 98.

For example, it may be desired for the user to have some information concerning the alignment between the external charger 50 and the IPG 100; the status of the IPG's battery 26, i.e., to what level it is charged; how much longer charging might take; the status of the external charger's battery 96; or the temperature of either the external charger 50 or the IPG 100. Temperature information can be particularly important to know for safety reasons, and can be provided by a thermocouple 101 in the external charger, and a thermocouple in the IPG (not shown). Inductive charging can heat both the external charger 50 and the IPG 100, and if temperatures are exceeding high, injury or tissue damage can result. Regardless, despite the importance of such charging information, the user interface 94 does not present such information to the user.

One approach in overcoming these shortcomings is disclosed in U.S. Patent Publication 2010/0305663 ("the '663 Publication"), filed Jun. 2, 2009, and incorporated herein by reference in its entirety. As shown in FIG. 5, the '663 Publication provides an RF communication link 210 between the external charger 50 and the external controller 12 so that they can communicate with each other. RF communication link 210 is enabled by an RF transceiver 202 and an RF antenna 202a in the external controller 12, and a corresponding RF transceiver 200 and antenna 200a in the external charger 50. Link 210 preferably comprises a Bluetooth™ compliant link, or other suitable RF communications protocol such as Zigbee™ WiFi, etc.

The external charger 50 and the IPG 100 can generate a variety of charging information such as those parameters just mentioned that can be transmitted to the external controller 12, where it can be reviewed and controlled by the external controller's 12 user interface 74, which as noted is more sophisticated and easier to view. For example, using RF communication link 210, the user can review the relevant charging information from the external charger 50. Relevant charging information from the IPG 100 such as battery 26 status and temperature can be transmitted via LSK link 176 to the external charger 50, and then sent to the external controller 12 via the RF communication link 210, or could be sent directly to the external controller 12 via FSK link 172. FIG. 6 shows the user interface 74 of the external controller 12 displaying such charging information 232 on its display 82. Some processing of the charging information may occur first in the external controller 12 before it is presented in this manner.

While the system of the '663 Publication provides desirable versatility, the inventors recognize a few drawbacks. For example, the system adds additional hardware components to the external charger 50 and the external controller 12 such as transceivers 200 and 202, antennas 200a and 202a, etc. This additional hardware adds cost, in terms of power and expense, and complexity to the system.

Given these shortcomings, the art of implantable medical devices would benefit from an improved means for providing relevant charging information to a patient, and this disclosure presents solutions.

DETAILED DESCRIPTION

The description that follows relates to use of the invention within a spinal cord stimulation (SCS) system. However, it is to be understood that the invention is not so limited. Rather, the invention may be used with any type of implantable medical device system. For example, the present invention may be used in a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator system configured to treat any of a variety of conditions.

Disclosed is an improved medical implantable device system including an improved external charger that is able to communicate with an external controller and IPG using the communication protocol (e.g., FSK) used to implement communications between the external controller and the implant. The external charger as modified uses its charging coil to charge the implant as is normal, and also to communicate with the other devices in the system. As such, the external charger is provided with transceiver circuitry operating in accordance with the protocol, and also includes tuning circuitry to tune the coil as necessary for communications or charging. Communication or charging access to the charging coil in the external charger is time multiplexed. The disclosed system allows charging information to be provided to the user interface of the external controller so that it can be reviewed by the user, who may take corrective action if necessary. Also disclosed are schemes for synchronizing and arbitrating communications between the devices in the system.

Figure 7:
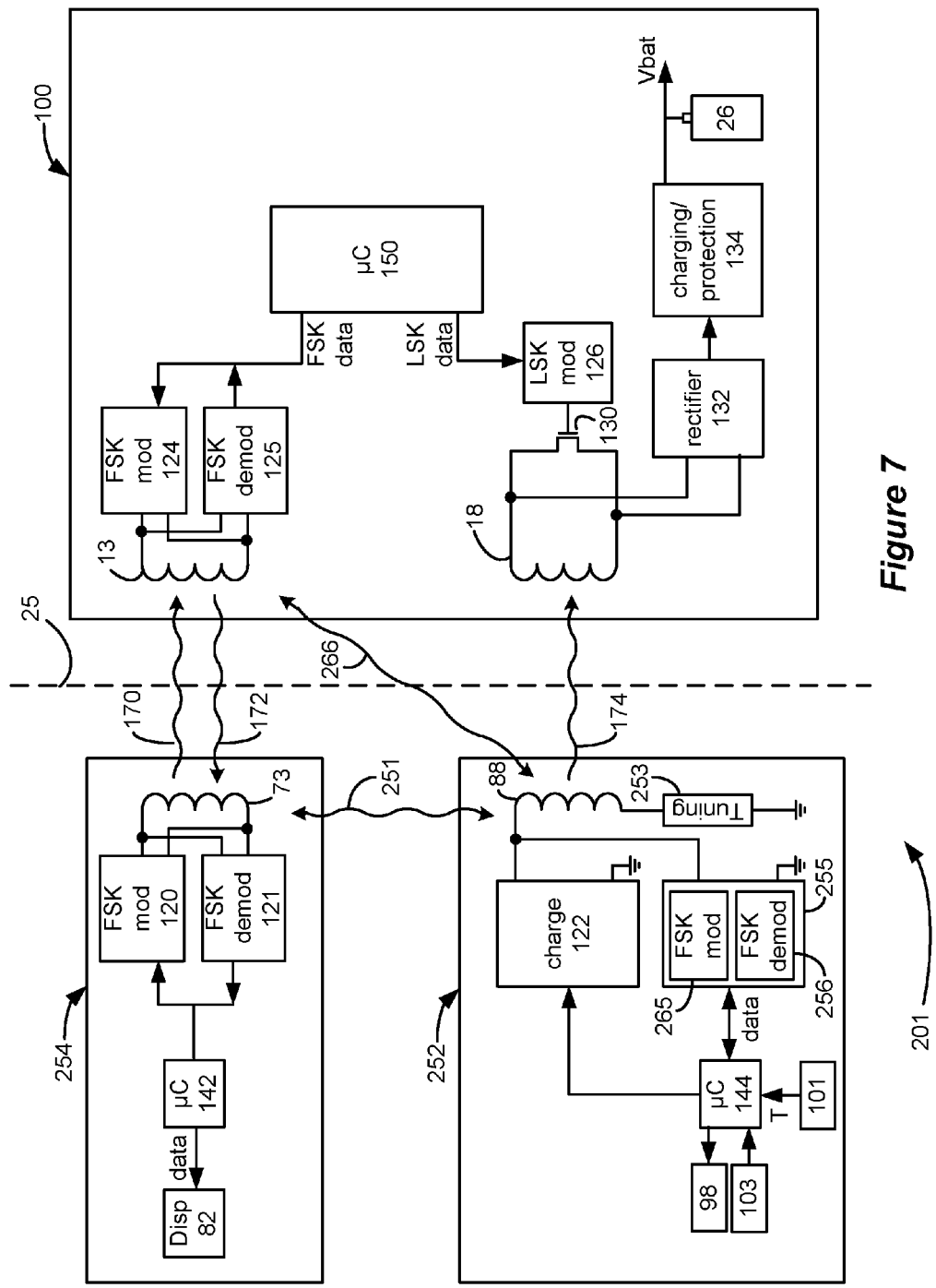
FIG. 7 shows an improved system in which the external controller and the external charger establish a communication link by using the charging coil of the external charger in accordance with an embodiment of the present invention.

FIG. 7 discloses an embodiment of the improved system 201, which system comprises an IPG 100, an improved external charger 252, and an improved external controller 254. Unlike previously-known approaches which use separate antennas and transceiver circuits for communicating data between the external charger and the external controller, the improved system 201 uses the charging coil 88 in the external charger 252 for communicating data to the external controller 254 via link 251. Link 251 preferably operates in accordance with the same protocol that is used by communication links 170 and 172 between the external controller 254 and the IPG 100, e.g., FSK. Additionally, because the coil 88 in the external charger 252 is FSK compliant, it may additionally communicate with the IPG 100 via an FSK link 266. Rendering the external charger 50 to be FSK compliant in this fashion requires only minimal changes to the external charger 50, and requires no hardware changes to either the external controller 254 or the IPG 100. Moreover, and as will be seen below, improving the communicative flexibility between these devices in system 201 allows charging information to be easily sent to the external controller 254, where such data can be processed and presented to the user interface 74 of the external controller.

Figure 4:
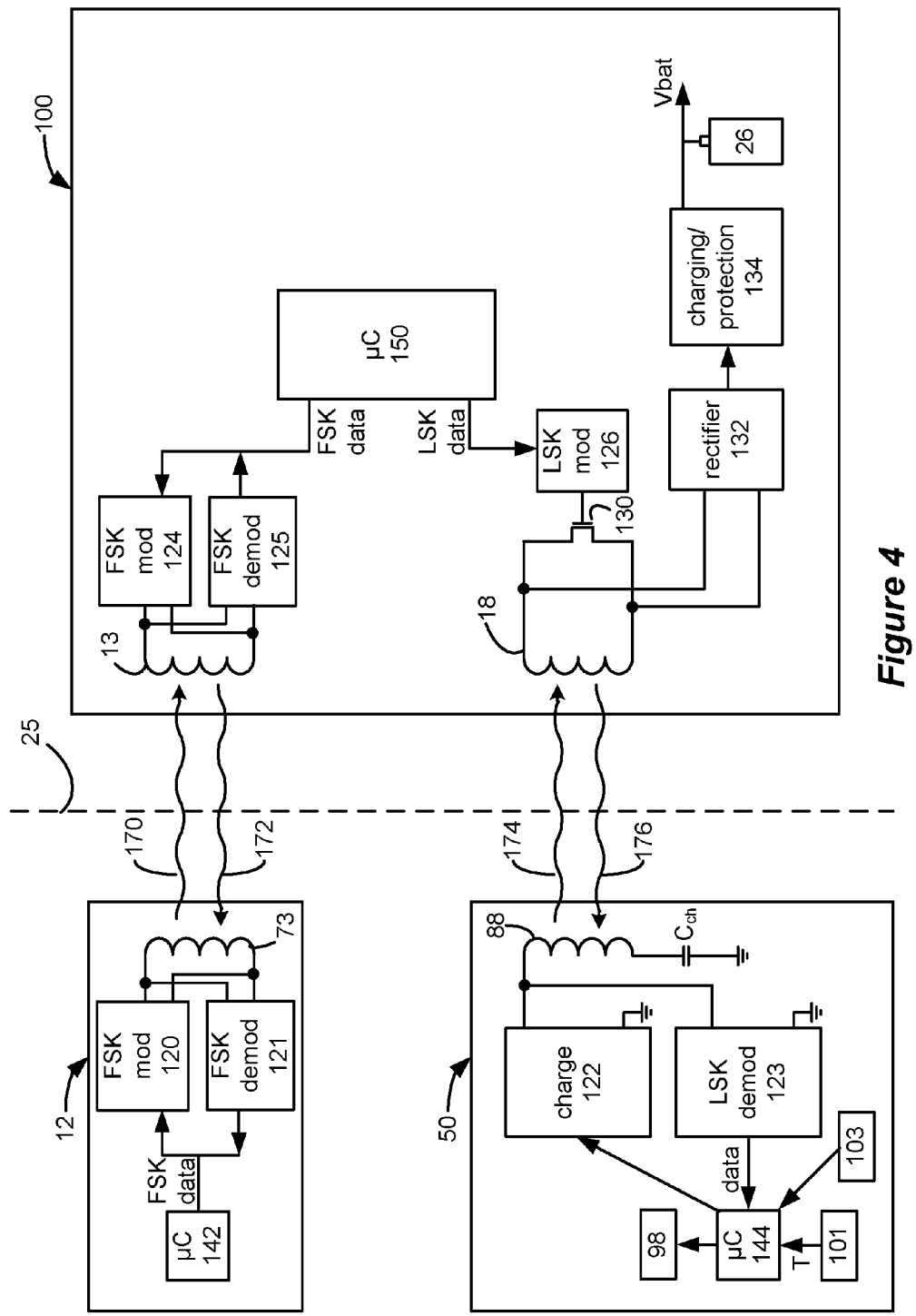
FIGS. 4 and 5 show communication circuitry present in the external controller, the external charger, and the IPG in accordance with the prior art.
Figure 5:
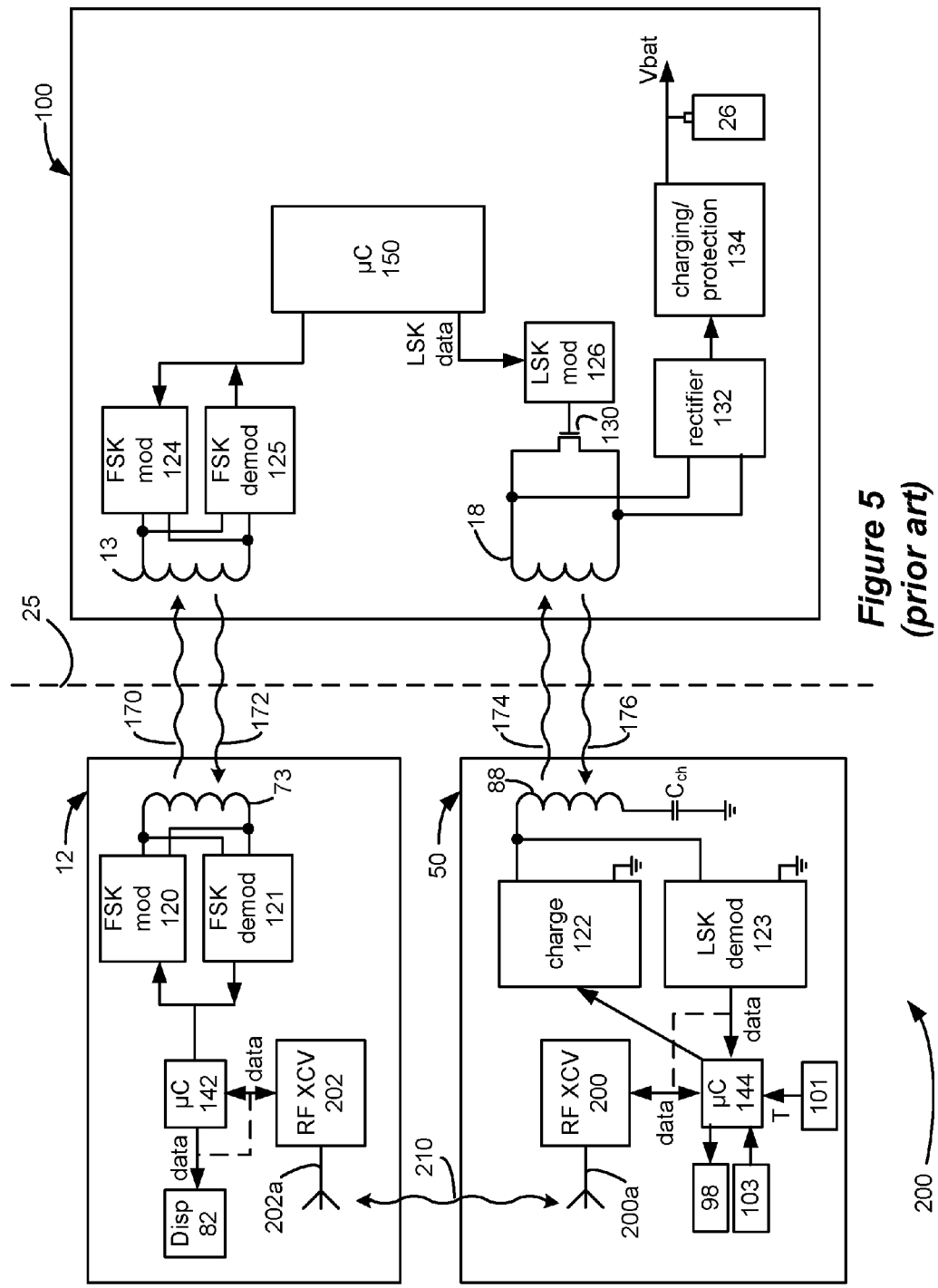

Legacy communications in system 201 remain unaffected. Thus, the external controller 254 and IPG 100 can still communicate via FSK via data links 170 and 172. And the external charger 252 can still provide a magnetic charging field (174) to the IPG 100. Moreover, the IPG 100 can still communicate data back to the external charger 252 via LSK, and as such the external charger 252 can still include LSK demodulation circuitry 123 (FIG. 4) if desired, although this is not shown in FIG. 7. As will be seen, there is less, or no, need in system 201 for LSK telemetry given the preferred use of FSK link 266 to communicate between the external charger 252 and the IPG 100.

The external charger 252 is modified in FIG. 7 to include a transceiver circuit 255, which includes a FSK modulator circuit 265, and a FSK demodulator circuit 256. The FSK modulator and demodulator circuits 265 and 256 can be similar to the FSK modulator and demodulator circuits 120 and 121 of the external controller 254. The external charger 252 also includes a tuning circuit 253 for tuning the coil 88 appropriately for both charging and FSK telemetry.

Figure 8:
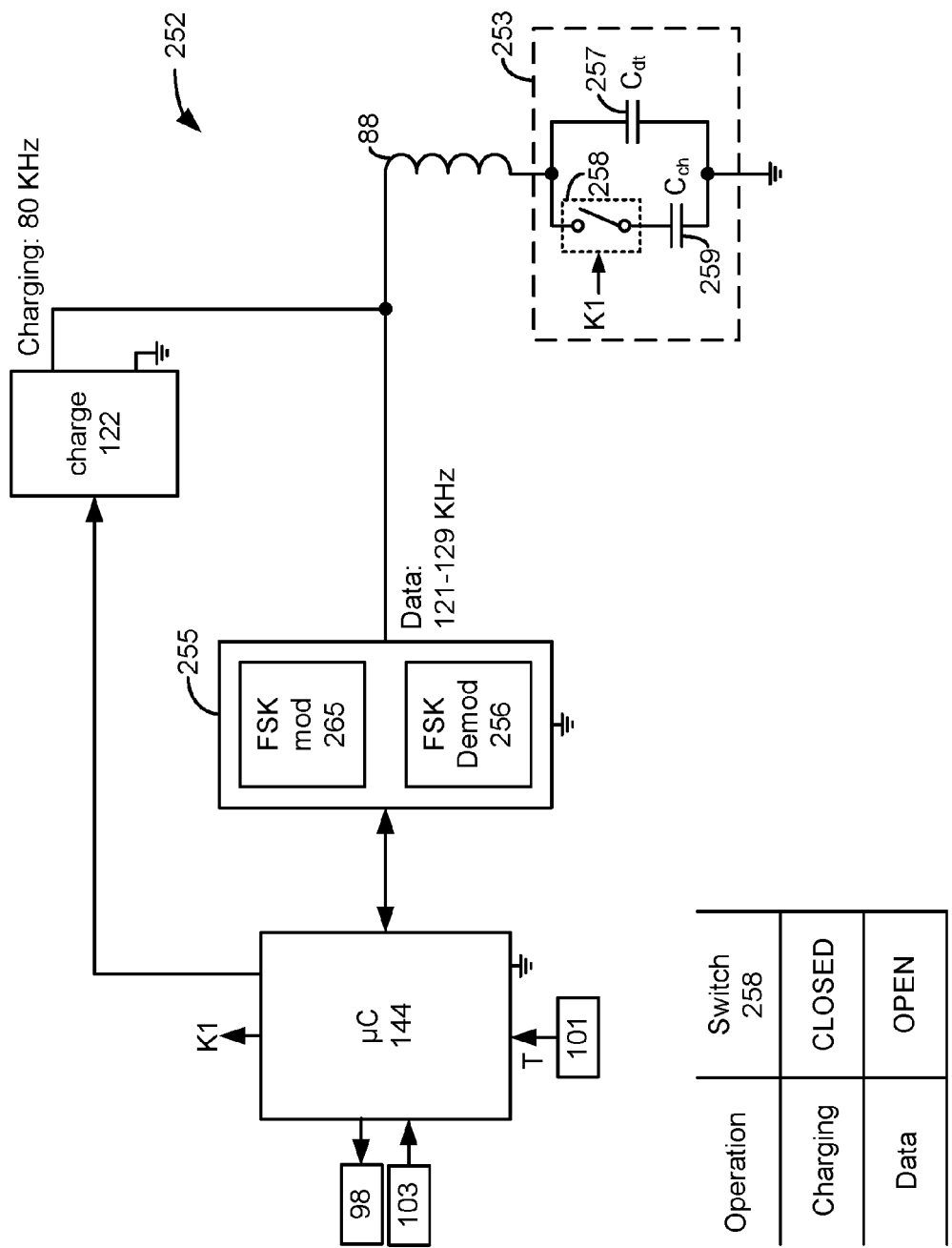
FIG. 8 shows additional details of the external charger of FIG. 7 in accordance with an embodiment of the present invention.

FIG. 8 illustrates the external charger 252 in further detail. Tuning circuit 253 includes charging capacitor Cch 259, a data capacitor Cdt 257, and a switch 258 controlled by a control signal K1 issued form the external charger's microcontroller 144. The series combination of the switch 258 and Cch 259 is connected in parallel with Cdt 257. Switch 258 can take one of two positions: open/off when the external charger 252 is being used to telemeter or receive data, and closed/on when it is being used to charge the IPG 100. When switch 258 is open during telemetry, Cch 259 is disconnected from the coil 88 resulting in a series resonant tank circuit formed by the coil 88 and Cdt 257 which resonates at a frequency suitable for FSK telemetry, e.g., 125 kHz. When switch 258 is closed, Cch 259 appears in parallel with Cdt 257, increasing the effective capacitance in series with coil 88 and lowering the frequency to that suitable for charging, e.g., 80 kHz.

Microcontroller 144 in the external charger 252 also controls charge circuit 122 and transceiver circuitry 255 at appropriate times, depending on whether charging or telemetry is taking place. For example, microcontroller 144 can turn off the charging circuit 122 or put it in high impedance state during data telemetry or during periods when the external charger 252 is listening for an incoming data transmission so that the charging circuit 122 does not load or affect the transceiver circuit 255. Likewise, the microcontroller 144 can turn off the transceiver circuit 255 or put it in high impedance state so that it does not load or affect the charging circuit 122 during charging. Although not shown, control signal K1 can also be received by charging circuitry 122 and transceiver circuitry 255 to inform those modules what mode (telemetry or charging) the external charger is operating in, and to respond appropriately.

While the external charger 252 is capable of carrying out data communication with the external controller 254, its primary purpose is to charge the IPG 100. Time spent by the external charger 252 in communicating with the external controller 254 or the IPG 100 is time spent not charging the IPG 100, which can result in longer charging times. Therefore, the external charger 252 is designed to maximize the amount of time spent charging the IPG 100, and only intermittently discontinues charging to communicate with the external controller 254 or the IPG 100 when necessary, as will be seen.

The external charger 252 can alternate between communicating telemetry data with the external controller 254 and charging the IPG 100 using two modes of operation: a fast data transmit mode, and a slow data transmit mode. The fast data transmit mode is particularly useful when the external charger 252 needs to provide near real-time charging information to the external controller 254. One example of this would be when the external charger 252 needs to provide alignment data to inform the user about the position of the external charger 252 relative to the IPG 100. It is desired to display such information relatively quickly on the display 82 of the external controller 254 so that the user can take quick corrective action in repositioning the external charger 252 if necessary. By contrast, other charging information, such as battery level, or alignment information once initial good alignment has been achieved, need not be presented at the external controller 254 as quickly, and instead this data can be uploaded to the external controller 254 in the slow data transmit mode with less frequency and with some latency, which is less disruptive of charging.

FIGS. 9A-9D illustrate timing diagrams to further describe the operation of system 201, and discusses in detail the data transmit modes just mentioned as well as other means of effecting communications between the external charger 252, the external controller 254, and the IPG 100. The timings illustrated in the Figures can be implemented and controlled by programming of the microcontrollers 144, 142, and 150 respectively in the external charger 252, the external controller 254, and the IPG 100. It should be noted that the various communication shown in FIGS. 9A-9D occur by FSK, either via FSK link 251 between the external charger 252 and the external controller 254, or link 266 between the external charger 252 and the IPG 100. Time-multiplexed access to the coil 88 in the external charger 252, and appropriate enablement of the charging circuitry 122, the FSK transceiver circuitry 255, and tuning circuitry 253, would occur as previously described. Timings for the various periods shown in FIGS. 9A-9D are shown at the bottom of each figure, but these are merely non-limiting examples. Timing may not be drawn to scale.

In the depicted example of the system 201, the external controller 254 takes precedence over the external charger 252, and can control the external charger 252 such as by turning the charger on or off, or requesting information from the charger as necessary. It is beneficial to arbitrate communications in this way because the charging field created by the external charger 252 (174, FIG. 7) can interfere with FSK communications. As such, when the external controller 254 wishes to communicate with either the external charger 252 or the IPG 100, the controller notifies the charger of that fact so that the charger can temporarily suspend production of the charging field.

Figure 9A:
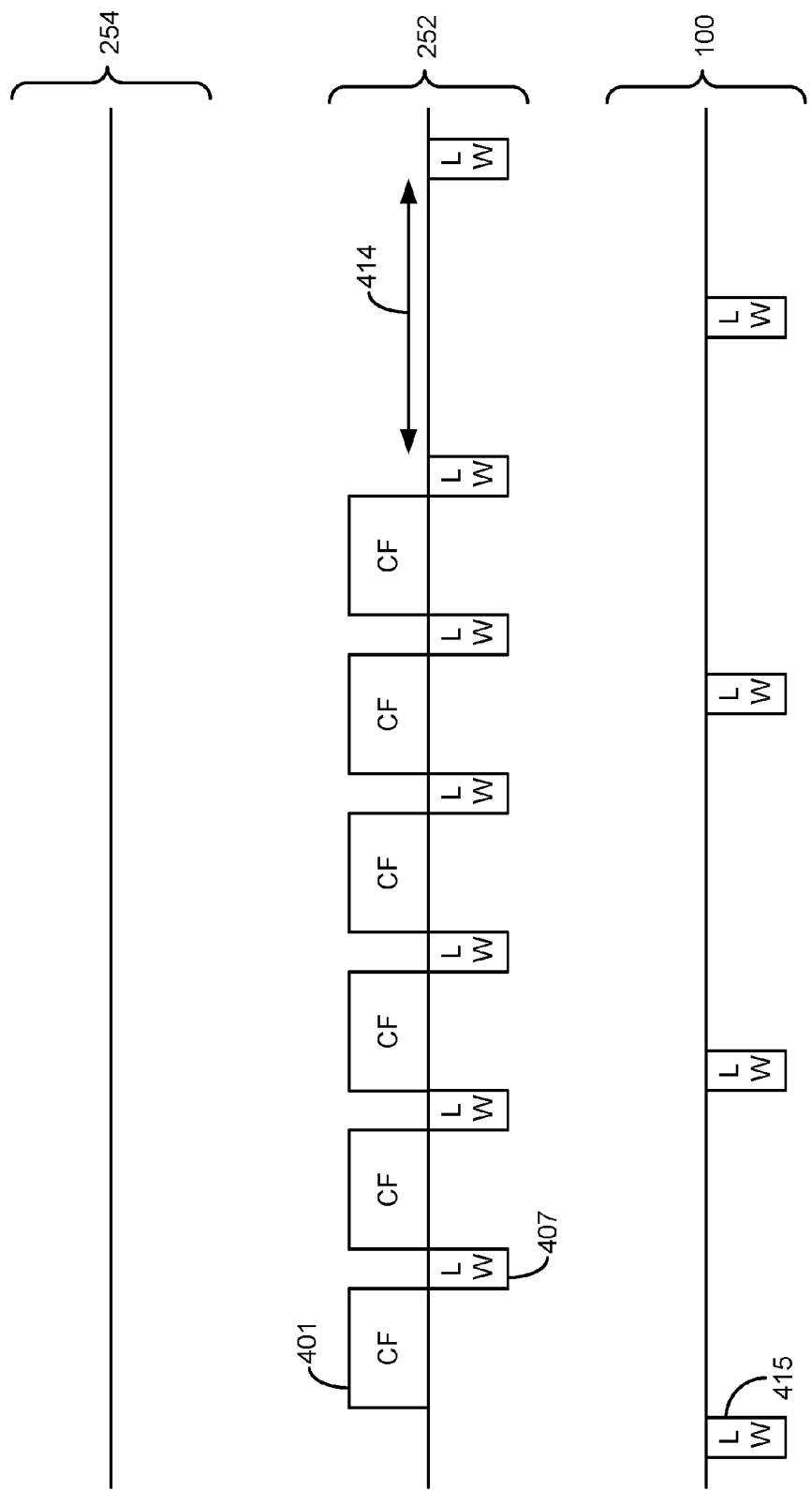
FIGS. 9A-9D show time-domain-multiplexed communications between the external charger, the external controller and the IPG of the system of FIG. 7 in accordance with an embodiment of the present invention.

As a result, the external charger 252 must periodically listen for communications from the external controller 254, as is shown starting in FIG. 9A. In FIG. 9A, the external charger 252 is operating as it does in a normal legacy system to provide a charging field. Thus, the patient has turned on the external charger 252 to produce a charging field to charge the battery 26 in the IPG 100. Such charging occurs during charging periods CF 401, which may last for a duration of 190 ms for example. Interspersed between these periods CF are listening windows LW 407, during which the external charger 252 listens for telemetry from external controller 254, which is not presently operating in FIG. 9A. The duration of the listening windows LW 407 may be 10 ms long in one example, which is small in comparison to the duration of the charging fields. Therefore, while the listening windows LW 407 increase the overall time needed to charge the battery 26 in the IPG 100, such interruptions are small, and generally transparent to the patient.

Figures 1A, 1B:
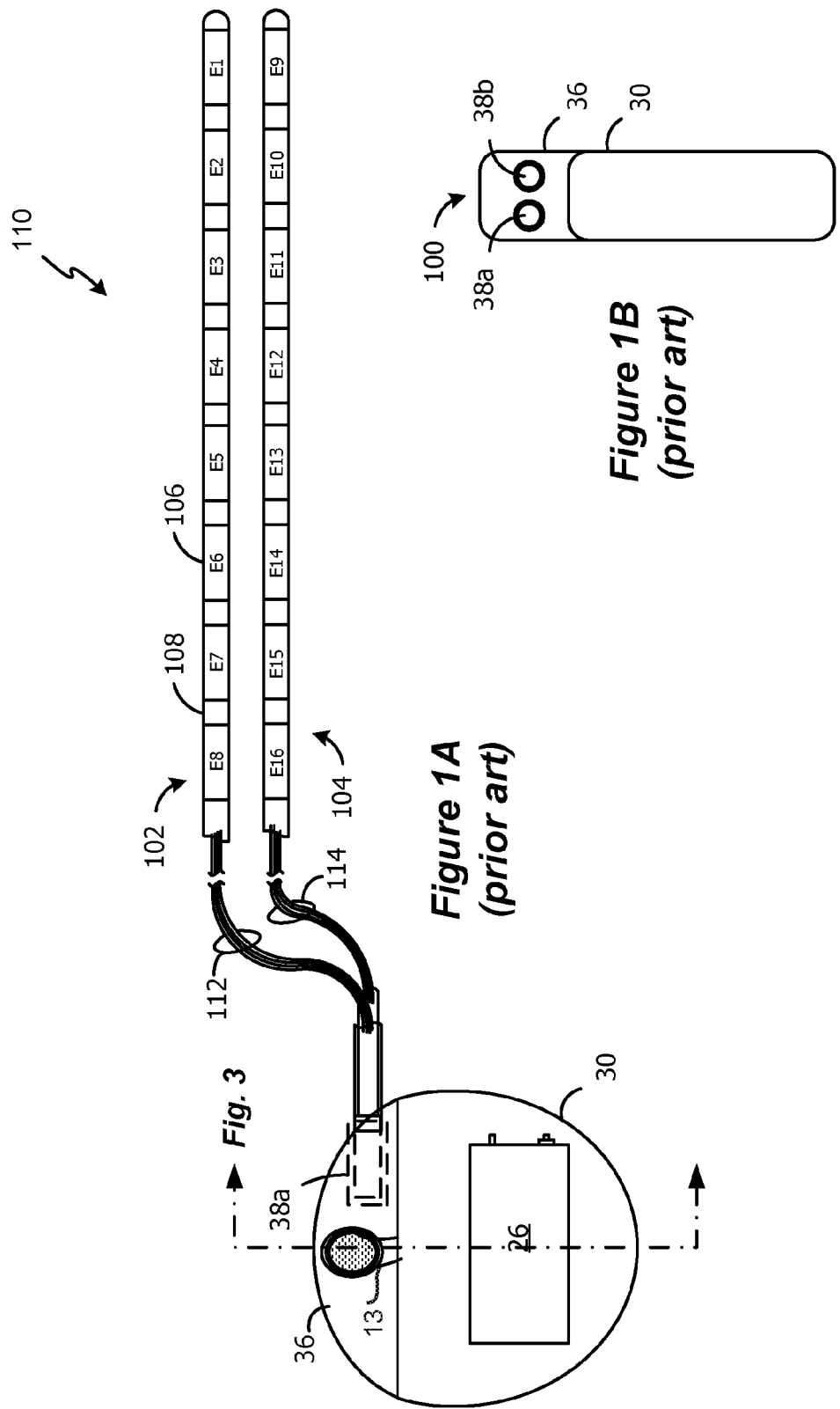
FIGS. 1A and 1B show an implantable pulse generator (IPG), and the manner in which an electrode array is coupled to the IPG in accordance with the prior art.
Figure 2:
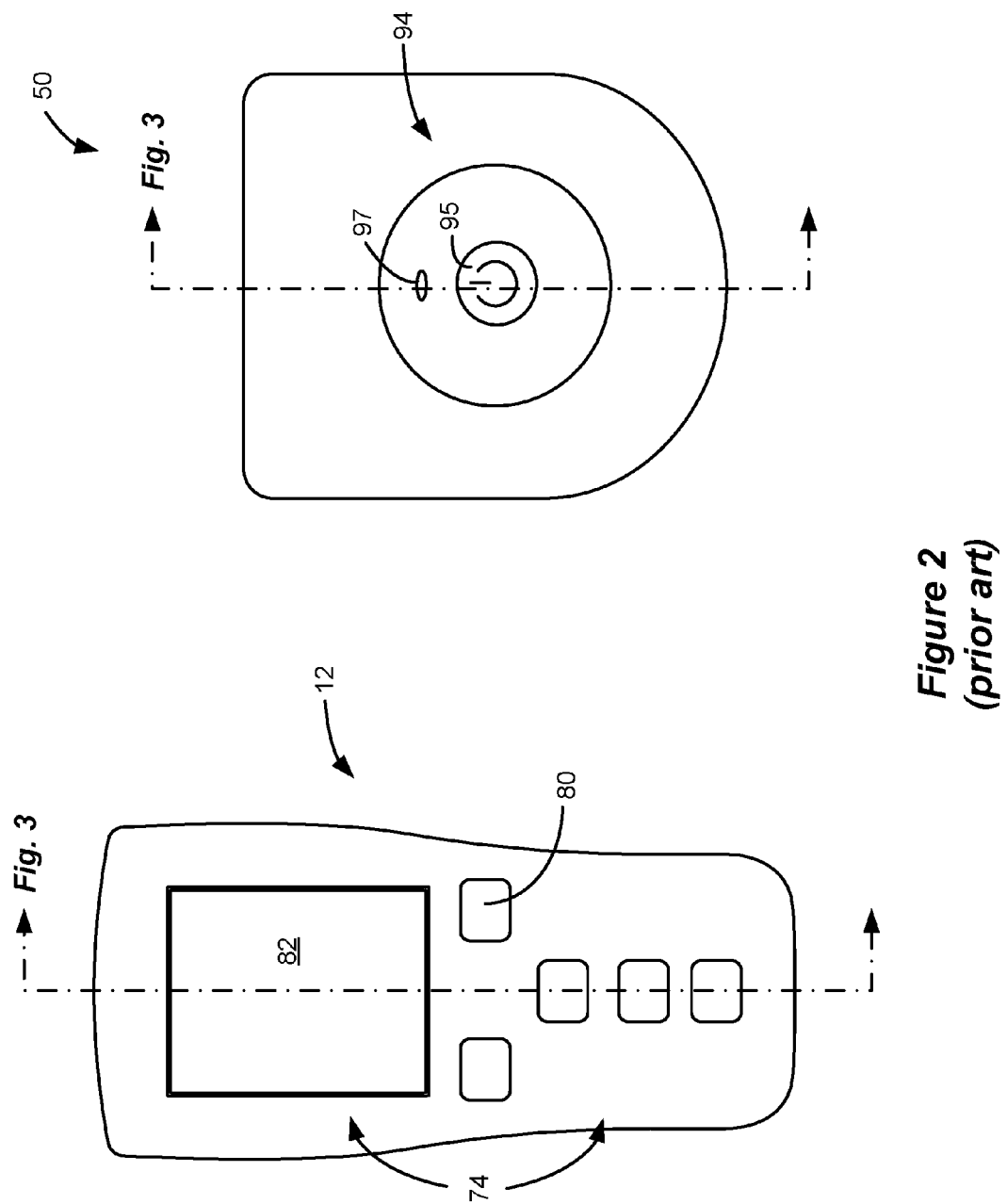
FIG. 2 shows plan views of an external controller and an external charger which communicate with an IPG in accordance with the prior art.
Figure 3:
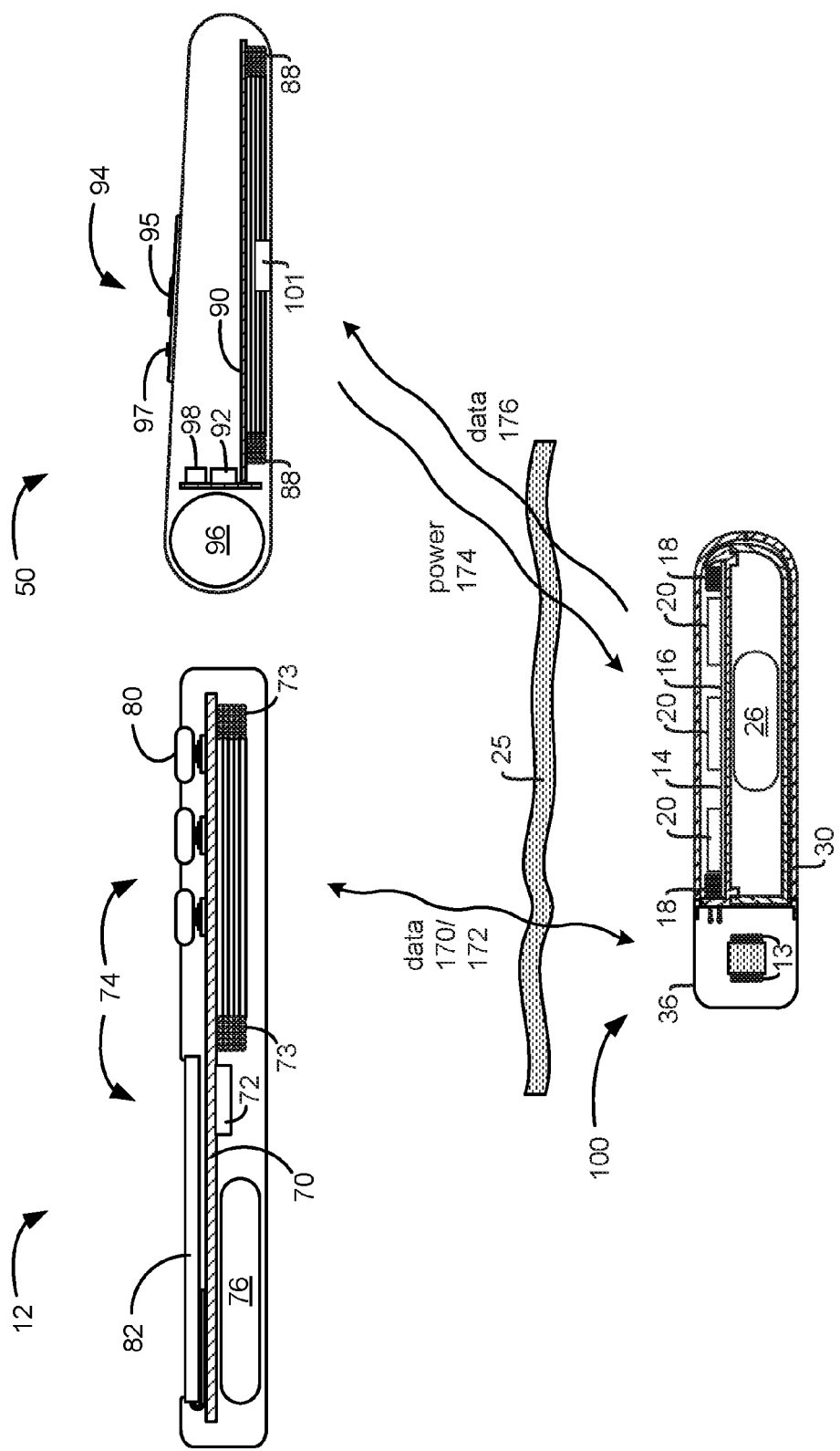
FIG. 3 shows cross sectional views of the external controller, the external charger and the IPG of FIGS. 1 and 2, and shows the communicative relations between these devices.

Eventually, the patient may turn off the external charger 252, or the charger may suspend charging per its normal operation when notified (by LSK telemetry for example) the battery 26 is fully charged, as shown by the absence of charging periods CF at the right side of FIG. 9A. At this point, the external charger 252 is in a power-down (low power, or sleep) state, but still periodically listens for telemetry from the external controller 254. Keeping the external charger 252 in a power-down state is reasonable given the relative large battery 96 (FIG. 3) within the charger. Once the external charger 252 is no longer producing a charging field, the spacing 414 between the listening windows LW 407 can be increased significantly to save power. Moreover, all the while, the IPG 100 has also been listening for telemetry requests during listening windows 415, as it does in legacy systems.

Figure 6:
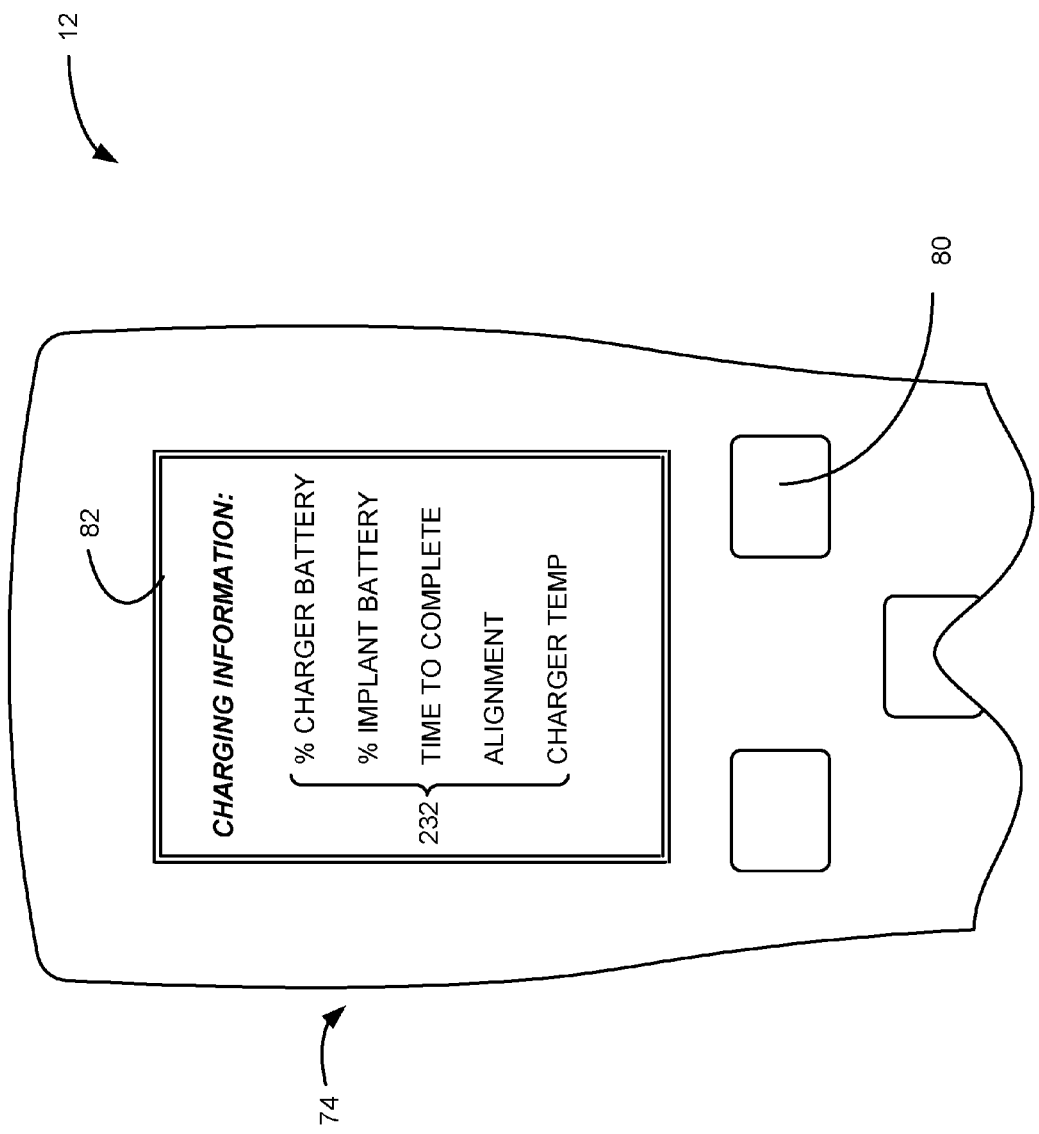
FIG. 6 shows the user interface of the external controller, and how that interface can display charging information in accordance with the prior art.
Figure 9B:
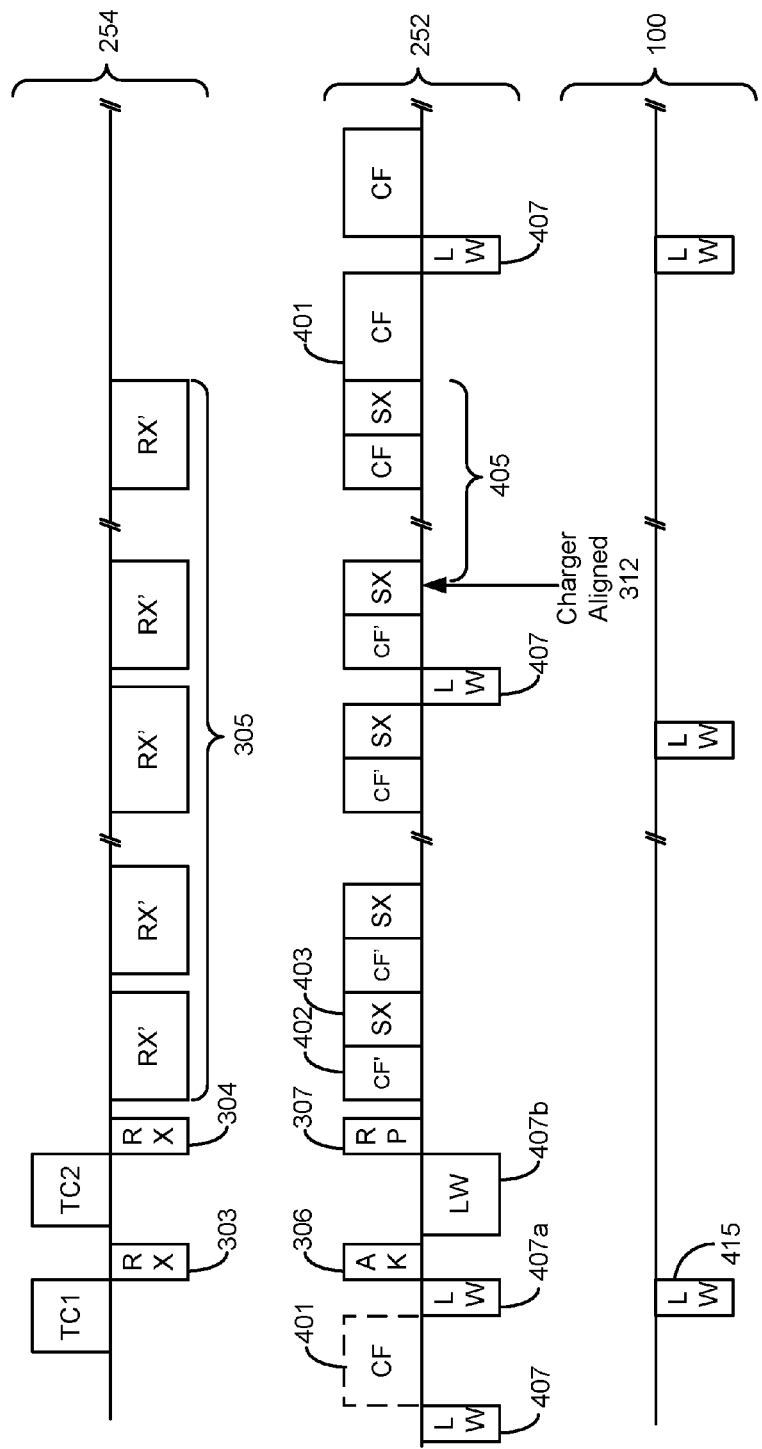

FIG. 9B illustrates use of the external controller 254 to receive charging information of the types previously discussed. Providing charging information to the external controller 254 can commence at any reasonable time during operation of the external controller 254, such as when the patient accesses an appropriate menu to review such information, as shown in FIG. 6 for example. Regardless of how or when this occurs, the external controller 254 transmits a first command TC1 to the external charger 252 along link 251 (FIG. 7), which in effect starts a "handshaking" procedure between the controller and charger. Prior to this, the external charger 252 may have been in the power-down state, or may have already been providing a charging field, as shown by the dotted line around period 401 at the left of FIG. 9B. If powered down, the external controller 254 will eventually turn on the external charger 252 so that it can produce a charging field and thus provide the charging information of interest, as will be seen shortly.

This first command TC1 requests an acknowledgment AK 306 from the charger 252, and alerts the external charger 252 to begin listening for further commands. The duration of TC1 is typically long enough to coincide with one of the external charger's listening windows LW, such as LW 407a in the illustrated example, and is repeated to ensure that it can be fully received during a window LW 407. The TC1 command can include in one example 19 bytes of alerting code recognizable by the external charger 252, 3 bytes of containing the device ID of the charger 252, 1 byte of command (in this case, requesting an acknowledgment), and two bytes of error checking code (e.g., Cyclic Redundancy Check (CRC) data). The device ID ensures that the proper device in the system—external charger 252—will respond as opposed to the IPG 100 or some other external charger or other external device.

The external charger 252 acknowledges receiving command TC1 with an acknowledgment AK 306, which is received at the external controller 254 during duration RX 303. AK 306 can also by default include status information, including the charging information, or such information may come later after handshaking. The external controller 254 then transmits another command, TC2, which instructs the external charger 252 to produce a charging field for charging the IPG 100, in case it is not providing one already. TC2 can be formatted similar to TC1 as just described. The external charger 252 receives command TC2 during listening window LW 407*b*, and replies with transmission RP 307. LW 407*b* can be longer than other listening windows as the external charger 252 is on notice that it will be receiving a possibly longer command TC2. RP 307 notifies the external controller 254 of the receipt of the command, as received during duration RX 304, and may again also include some status information.

As noted earlier, the external charger 252 can operate in fast data transmit mode or in slow data transmit mode, which mode of operation, in one example, can be determined based on the level of alignment between the external charger 252 and the IPG 100. In the example provided in FIG. 9B, the external charger 252 begins operation in the fast data transfer mode as a default once it has handshaken with the external controller 254 in the manner just described. This is preferred even if the external charger 252 is already well aligned with the IPG 100, i.e., if alignment circuitry 103 already indicates sufficient alignment, which it very well may be if it were already providing a charging field to the IPG 100 (FIG. 9A). If alignment is already sufficient, or if alignment is achieved quickly, then the system will not remain the fast data transfer mode for long, as will be described below.

In fast data transmit mode, the external charger 252 alternates between periods CF' 402 and SX 403, each with relatively equal duration. During periods CF' 402, the external charger 252 charges the IPG 100 by producing a magnetic charging field at coil 88, and in state SX 403 it transmits charging information, such as alignment information provided from alignment circuitry 103 and possibly other charging parameters already mentioned, to the external controller 254. The external controller 254 receives this information during periodic receives periods RX' 305, which correspond with the SX transfers from the external charger 252. The external controller 254 can infer from the received alignment information whether the external charger 252 is operating in a fast data transmit mode, and accordingly can schedule the receive period RX' 305 at appropriate times so that data transfer during states SX is synchronized. Alternatively, the SX transmission can specifically include an indication of the external charger 252's data transfer mode.

Once the charging information is received at the external controller 254, it can be processed if necessary and forwarded to the display 82 device for user review. By alternating relatively rapidly between CF and SX, the external charger 252 provides near-real-time alignment information to the user, which allows the user to take quick responsive action to try and better position the external charger 252 relative to the IPG 100. Although during the fast data transmit mode charging of the IPG battery 26 would be twice as slow, this mode should not last for long, and the battery 26 is still being charged to some degree.

Eventually, the user will be able to align the external controller 254 with the IPG 100, which is indicated in FIG. 9B at time 312. At this point, the fast data transmit mode between the external charger 252 and external controller 254 could cease, and a slow data transmit mode entered. However, in the illustrated example, these devices continue to operate in fast data transmit mode during period 405 to account for any additional movement by the user to fine tune the alignment, which can be on the order of seconds. During period 405, alignment circuitry 103 can continue to be checked by the external charger 252 to ensure that good alignment continues to be established, and that the fast data transfer mode can eventually be left. After period 405, the external charger 252 enters the slow data transmit mode, and the external controller 254 stops listening for SX, and thus receive periods RX' 305 are no longer present. Again, the external controller 254 will know based on the received alignment information when the external charger 252 has left the fast data transfer mode and when period 405 has ceased.

Figure 9C:
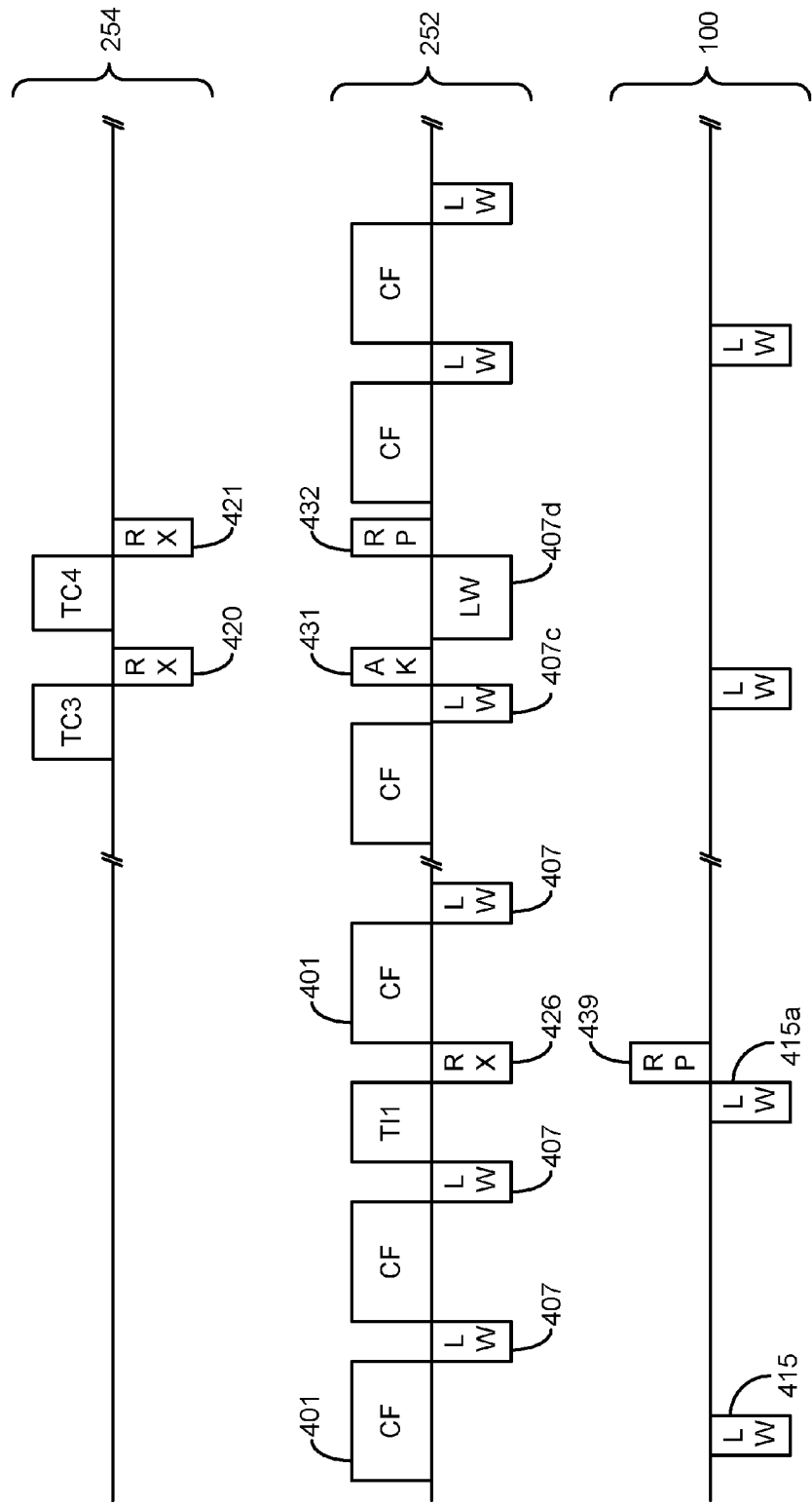

After period 405, the external charger 252 enters the slow data transmit mode as just noted, which is illustrated in FIG. 9C. In slow data transmit mode, the external charger 252 continues charging the IPG 100 during periods CF 401, but continues periodically listening for any telemetry from the external controller 254 during listening windows LW 407. The external charger 252 also requests relevant charging information from the IPG 100, such as its battery level and temperature. Eventually, the external charger 252 will package the IPG's charging information with the external charger's charging information to the external controller 254.

Procuring IPG charging information occurs by external charger 252 transmitting a command TI1 to the IPG 100 along link 266 (FIG. 7). The duration of TI1 is typically long enough to coincide with one of the IPG's listening windows LW, such as LW 415*a* in the illustrated example, and is repeated to ensure that it can be fully received during a listening window LW 415. The TI1 command can include in one example 19 bytes of alerting code, 3 bytes containing device ID of the IPG 100, 1 byte of command requesting status information, and 2 bytes of error correcting code (e.g., CRC)—similar to the commands sent from the external controller 254 to the external charger 252 (FIG. 9B).

Upon receiving the TI1 command, the IPG 100 transmits a reply RP 439, which includes the required IPG charging information. Synchronization of this reply 439 and receipt 426 at the external charger 252 can be ensure by having the IPG 100 extended listening window until it no longer receives any data, i.e., when the end of command TI1 is sensed. The external charger 252 can store the charging information received from the IPG 100 in memory. The external charger 252 can repeatedly query the IPG 100 to update the stored charging information. It is preferred for simplicity that data transfer between the external charger 252 and the IPG 100 occur in this manner illustrated, instead of implementing a handshaking/acknowledgment/reply type scheme as used between the external controller 254 and the external charger, although this more-complicated scheme could also be used. After receiving the charging information from the IPG 100, the external charger 252 can return to charging the IPG 100 by continuing to intersperse charging filed periods CF 401 and listening windows 407.

Eventually, the external controller 254 will request charging information from the external charger 252, although because the system 201 is now operating a slow data transmit mode, this may occur more sporadically, e.g., even ten seconds or so. To transfer the charging information, the external controller 254 sends command TC3 and TC4 to the external charger 252 coincident with listening windows LW 407*c* and 407*d*. This handshake and data exchange is similar to that described earlier with respect to commands TC1 and TC2, and so such details are not repeated here. In any event, the external charger's reply 432 provides the charging information—both the external charging information and the IPG charging information—to the external controller during RX 421. Again, this transmission occurs more slowly, but sufficiently quickly to update the display 82 in the external controller with the relevant charging information. After this, the external charger 252 can continue charging (401) and listening (407) as before.

If at any time during the slow data transmit mode the external charger 252 becomes misaligned with the IPG 100, such would be reported by the alignment circuitry 103 in the external charger 252, and would eventually be reported to the external controller 254. As such, the external controller 254 can once again instigate the fast transmission mode via commands TC1 and TC2 as described earlier with respect to FIG. 9B.

Figure 9D:
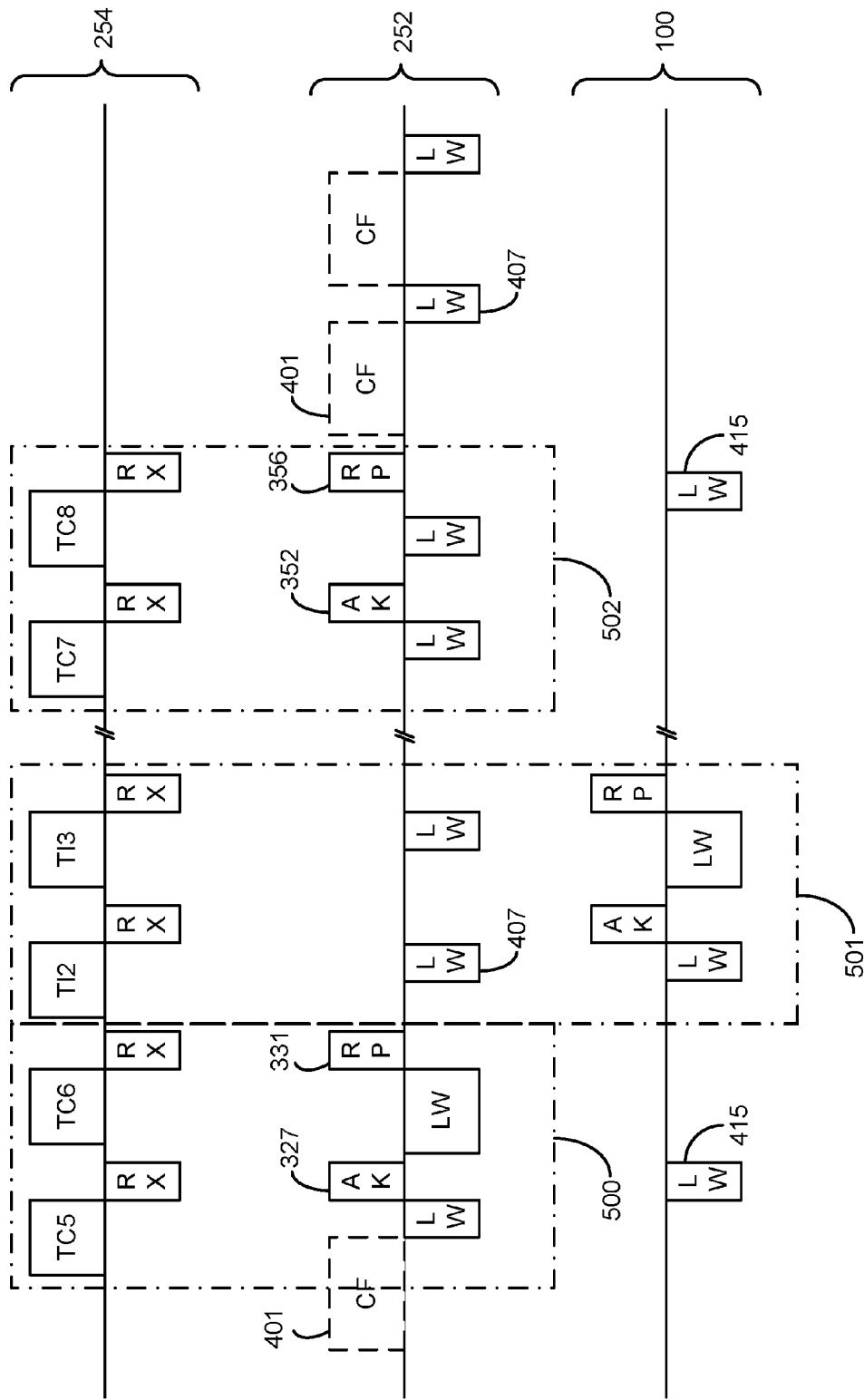

FIG. 9D shows control of the external charger 252 when the external controller 254 needs to communicate data with the IPG 100, as is its legacy function. This could occur for example if the patient is trying to change the therapy being provided by the IPG 100. In this circumstance, the external controller 254 may not necessarily know if the patient is currently operating his external charger 252 to charge the IPG's battery. As mentioned earlier, the charging field produced by the external charger 252 may interfere with FSK communications between the external controller 254 and the IPG 100. As such, having the charging field activated during communications between the external controller 254 and the IPG 100 is unadvisable. One way of getting around this problem would be to alert the user to manually shut off the external charger 252 before beginning communications between the external controller 254 and the IPG 100. But this puts additional operational burden on the user.

FIG. 9D illustrates a solution in which prior to communications with the IPG 100, the external controller 254 will instruct the external charger 252 to shut off, and then to turn back on if necessary, i.e., if the charger was operating in the first place. Because the external controller 254 automatically shuts off operations of external charger 252, it is no longer necessary for the user to manually discontinue charging before beginning communications between the external controller 254 and the IPG 100. This makes operation by the user much simpler while at the same time ensuring that there is no interference. In a preferred embodiment, the external controller 254 always sends at least one command to suspend the external charger 252 before communicating with the IPG 100, even if it is unnecessary because the charger 252 is not currently engaged.

In FIG. 9D, the external controller 254 suspends operation of the external charger 252 during period 500; communicates with the IPG 100 during period 501; and recommences charging (if necessary) in period 502. In period 500, the external charger sends commands TC5 and TC6 to the external charger to suspend charging, which occurs in the same manner as commands TC1 and TC2 describes previously (FIG. 9B). The external charger 252 can confirm that it has suspended charging in reply 331. If the external charger 252 is not currently engaged in charging, it may additionally inform the external controller 254 of that fact in reply 331. If the external charger 252 is not present at all, e.g., if it is distant from the patient and out of communication reach, then no acknowledgment AK 327 is received at the external controller 254, which can then simply begin communications with the IPG 100 during period 501.

While period 500 in FIG. 9D only shows the external controller 254 shutting down the charging field 401, it is understood that similar instructions TC5 and TC6 can be used to shut down any operation that the external charger 252 is carrying out with the IPG 100. For example, if the external charger 252 were in the process of requesting charging information from the IPG 100 (as shown by command TI1 in FIG. 9C), the external controller 254 will automatically shut off any FSK communication between the external charger 252 and the IPG 100 during the time that the external controller 254 wants to communicate with the IPG 100.

In period 501, the external controller 254 communicates with the IPG 100, using commands TI2 and TI3, and the type of handshaking procedure already discussed. Alternatively, communications between the external controller 254 and IPG 100 can take place in any manner as they occur in legacy systems. Typically, commands sent from the external controller to the IPG 100 represent some information that the external controller 254 wants to send to the IPG 100. Such information can relate to status inquiries, wake up messages, power down messages, turning stimulation on/off, level or amplitude of stimulation pulses, duration or frequency of stimulation pulses, selection of electrodes to be activated, etc. The external controller 254 will compile this information into appropriate commands (such as TI2 and TI3) that can be understood by the IPG 100. Of course, the exact format of the commands will correspond to the type of IPG 100. Communication between the external controller 254 and the IPG 100 can also include information transmitted from the IPG 100 to the external controller 254. Two examples of such communication are shown by way of messages AK and RP in period 501.

Once these communications are complete, the external controller 254 can once again instruct the external charger 252 to commence charging during period 502. Once again, this can occur using commands TC7 and TC8 and the handshaking procedure already discussed. However, it is not strictly necessary to issue commands TC7 and TC8 to recommence charging. For example, if the external charger 252 was not producing a charging field, which would be evident based on a lack of an acknowledgment 327 or an indication of no charging in the reply 331, the external controller 254 may dispense with sending commands to recommence charging during period 502. In fact, this may be preferred to prevent unwanted engagement of the external charger 252. Alternatively, it may be harmless to send the commands TC7 and TC8 to recommence charging in any event: if the external charger 252 is out of range, such commands will once again simply not be acknowledged (352); if the external charger 252 was not previously engaged in charging—for example, if the charger had not been turned on by the user—it can choose to simply ignore the commands. If the external charger 252 was engaged in charging, it can confirm recommencement of charging to the external controller 254 in reply 356, and can continue providing charging information to the external controller 254 in the manners previously described.

Although not shown in FIG. 9D for simplicity, it should be understood that commands TC7 and TC8 may instruct the external charger 252 to enter the default fast data transmit mode. This might be beneficial to ward again the possibility that the external charger 252 became misaligned while it was suspended during period 501, a problem better handled during the fast mode as described earlier.

Although discussed in the context of providing charging information to the external controller 254, it should be recognized that the communicative flexibility provided by modifications to the external charger 252, and the FSK links 251 and 266 it supports, can be put to other beneficial uses in the system 201. This disclosure should therefore not be limited in its applicability to that context.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for operating an implantable medical device system, comprising:
charging an implantable medical device with a charging field generated from a coil in an external charger;
determining, using circuitry in the external charger, a degree of alignment between the external charger and the implantable medical device; and
communicating, using the coil in the external charger, with an external controller,
wherein a ratio of time that the coil is used for the act of communicating to time that the coil is used for the act of charging is based on the degree of alignment between the external charger and the implantable medical device.

2. The method of claim 1, wherein the ratio is greater when the degree of alignment between the external charger and the implantable medical device is lower.

3. The method of claim 1, wherein the act of communicating comprises sending charging information to the external controller.

4. The method of claim 3, further comprising conveying the charging information to a user via a user interface of the external controller.

5. The method of claim 4, wherein the user interface is a graphical user interface.

6. The method of claim 1, wherein the act of communicating comprises operating in one of two data transmit modes, comprising:
a fast data transmit mode; and
a slow data transmit mode, wherein the ratio is smaller in the slow data transmit mode than in the fast data transmit mode.

7. The method of claim 6, wherein the act of communicating comprises initializing communications between the external charger and the external controller.

8. The method of claim 7, wherein the act of communicating comprises defaulting to the fast data transmit mode after the communications are initialized.

9. The method of claim 8, wherein the act of communicating comprises transitioning to the slow data transmit mode when a predetermined degree of alignment is observed.

10. The method of claim 6, wherein the act of communicating comprises sending information regarding the alignment between the external charger and the implantable medical device in the fast data transmit mode.

11. The method of claim 1, wherein the act of communicating comprises periodically interrupting the act of charging to listen for communications from the external controller.

12. An implantable medical device system, comprising:
an implantable medical device;
an external controller for communicating with the implantable medical device; and
an external charger comprising a coil, the external charger configured to:
generate a charging field, using the coil, for providing energy to the implantable medical device;
determine a degree of alignment between the external charger and the implantable medical device; and
periodically suspend generation of the charging field to communicate with the external controller using the coil, wherein a ratio of time during which generation of the charging field is suspended to time that the charging field is being generated is based on the degree of alignment between the external charger and the implantable medical device.

13. The system of claim 12, wherein the ratio is greater when the degree of alignment between the external charger and the implantable medical device is lower.

14. The system of claim 12, wherein the external charger is configured to communicate charging information to the external controller during the suspension of the generation of the charging field.

15. The system of claim 14, wherein the charging information comprises information regarding the degree of alignment between the external charger and the implantable medical device.

16. The system of claim 12, wherein the external charger comprises a tuning circuit coupled to the coil, wherein the tuning circuit is configured to tune the coil to a first frequency for generating the charging field and a second frequency for communicating with the external controller.

17. The system of claim 12, wherein the external charger is configured to generate the charging field and to periodically suspend generating the charging field in accordance with one of two operational modes, comprising:
a fast data transmit mode; and
a slow data transmit mode, wherein the ratio is smaller in the slow data transmit mode than in the fast data transmit mode.

18. The system of claim 17, wherein the external charger is configured to communicate information regarding the degree of alignment between the external charger and the implantable medical device using the fast data transmit mode.

19. The system of claim 17, wherein the external charger is configured to communicate charging information to the external controller using the slow data transmit mode.

20. The system of claim 19, wherein the external controller comprises a user interface for conveying the charging information to a user.

* * * * *